US00PP27221P3

(12) United States Plant Patent
Kordes

(10) Patent No.: US PP27,221 P3
(45) Date of Patent: Oct. 4, 2016

(54) MINIATURE ROSE PLANT NAMED 'KORPOT040'

(50) Latin Name: *Rose hybrida*
Varietal Denomination: KORpot040

(71) Applicant: W. KORDES' SÖHNE ROSENSCHULEN GMBH & CO KG, Offenseth-Sparrieshoop (DE)

(72) Inventor: Tim-Hermann Kordes, Offenseth-Sparrieshoop (DE)

(73) Assignee: W. KORDES' SÖHNE ROSENSCHULEN GMBH & CO KG, Offenseth-Sparrieshoop (DE)

( * ) Notice: Subject to any disclaimer, the term of this patent is extended or adjusted under 35 U.S.C. 154(b) by 107 days.

(21) Appl. No.: 14/544,598

(22) Filed: Jan. 26, 2015

(65) Prior Publication Data

US 2015/0223375 P1 Aug. 6, 2015

Related U.S. Application Data

(60) Provisional application No. 61/965,484, filed on Jan. 31, 2014.

(51) Int. Cl.
*A01H 5/02* (2006.01)

(52) U.S. Cl.
USPC ..... Plt./122

(58) Field of Classification Search
USPC ..... Plt./116, 122
See application file for complete search history.

*Primary Examiner* — Susan McCormick Ewoldt
(74) *Attorney, Agent, or Firm* — Barbara Campbell; James M. Weatherly; Cochran Freund & Young, LLC

(57) ABSTRACT

A new and distinct variety of rose with long lasting, red flowers, and attractive foliage with above-average disease resistance; the new variety exhibits compact, upright to bushy growth with abundant flowers; and the new variety propagates well from cuttings and by grafting.

2 Drawing Sheets

Genus and species: *Rosa hybrida.*
Denomination: 'KORpot040'.

BACKGROUND

'KORpot040' originated from a controlled crossing in a breeding program of two distinct parents during the summer of 2010 in a controlled environment in Offenseth-Sparrieshoop, Germany between an un-named *Rosa hybrida* seedling as the seed or female parent (unpatented) and another un-named *Rosa hybrida* seedling as the pollen or male parent (unpatented).

The objective of the cross/hybridization was to create a new and distinct rose plant with unique qualities, such as:

1. Compact and uniform growth and flowering under greenhouse conditions when grown as a potted floral plant;
2. Abundant, long lasting, and attractive flowers and foliage;
3. Resistance to diseases encountered in greenhouse and nursery culture; and
4. Suitability for production from softwood cuttings in floral and nursery containers.

The resulting seeds from the cross were planted during the following winter in 2010 and were evaluated. The resulting seedlings exhibited distinctive physical and biological characteristics. 'KORpot040' was selected in April 2011 as a single plant from the seedling beds in Offenseth-Sparrieshoop, Germany due to its superior characteristics. 'KORpot040' was first asexually propagated by rooting softwood cuttings in June 2011 at a nursery in Offenseth-Sparrieshoop, Germany and asexually propagated for further evaluation. This new and distinctive rose variety was subsequently named 'KORpot040'.

The initial and other subsequent asexual propagations were conducted in controlled environments and demonstrate that 'KORpot040' reproduces true to type in successive generations of asexual reproduction via rooting softwood cuttings.

CROSS REFERENCE TO RELATED APPLICATIONS

Plant Breeder's Right for 'KORpot040' were applied for with the European Community Plant Variety Office on Feb. 6, 2014, File No. 2014/0282. 'KORpot040' has not been made publicly available or sold more than one year prior to the priority date of this application.

SUMMARY

The following are the most outstanding and distinguishing characteristics of this new variety when grown under normal horticultural practices in Jackson County, Oreg.

1. 'KORpot040' has dark red, medium sized flowers, which have good durability; and
2. 'KORpot040' has a compact, upright to bushy habit.

DESCRIPTION OF THE PHOTOGRAPHS

This new miniature rose plant is illustrated by the accompanying photographs which shows an overall view of the plant and individual parts of the plant. The colors shown are as true as can be reasonably obtained by conventional photographic procedures.

DETAILED DESCRIPTION

Figure 1:
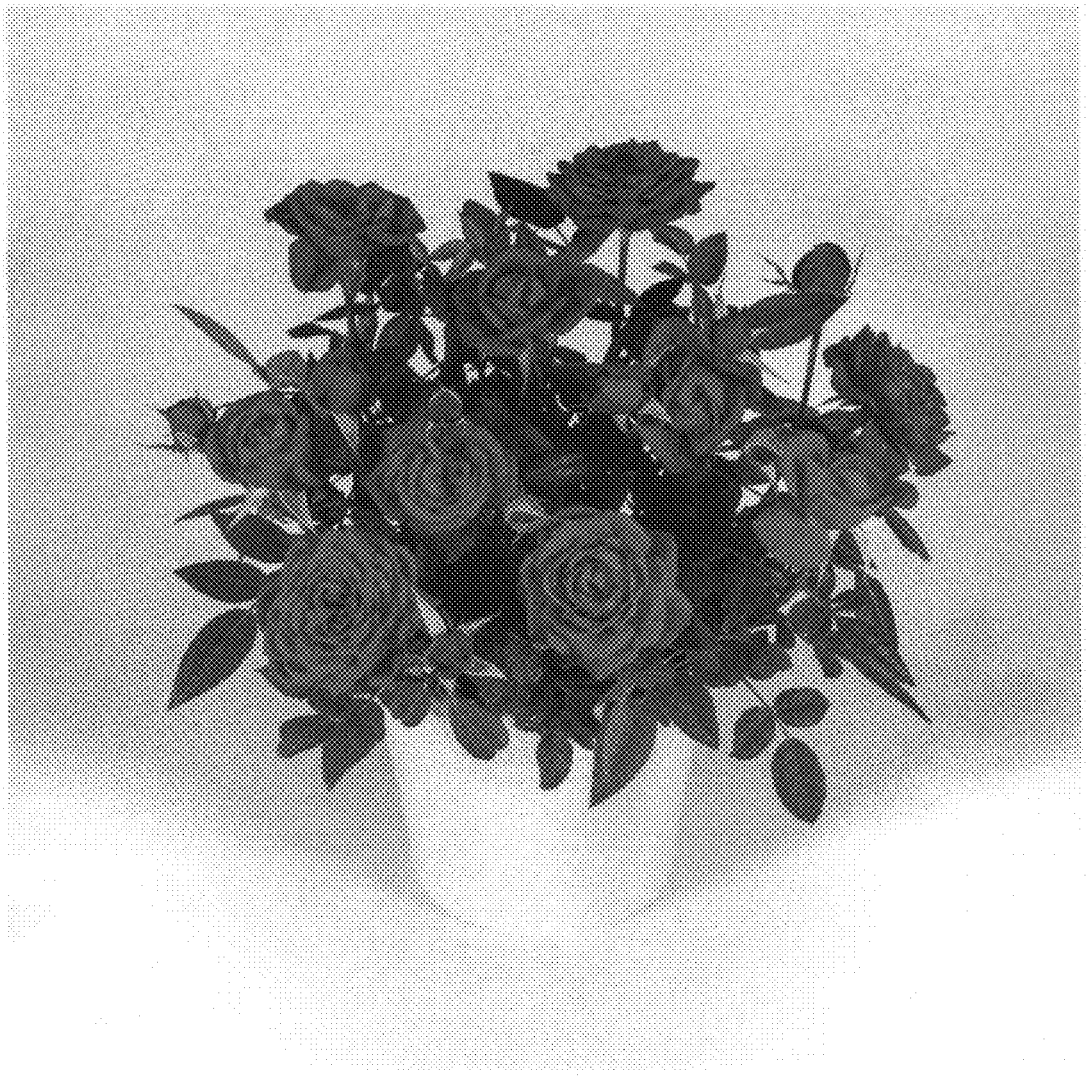
FIG. 1 shows a whole plant approximately 4 months of age and grown in a glasshouse in a nursery in Offenseth-Sparrieshoop, Germany.
Figure 2:
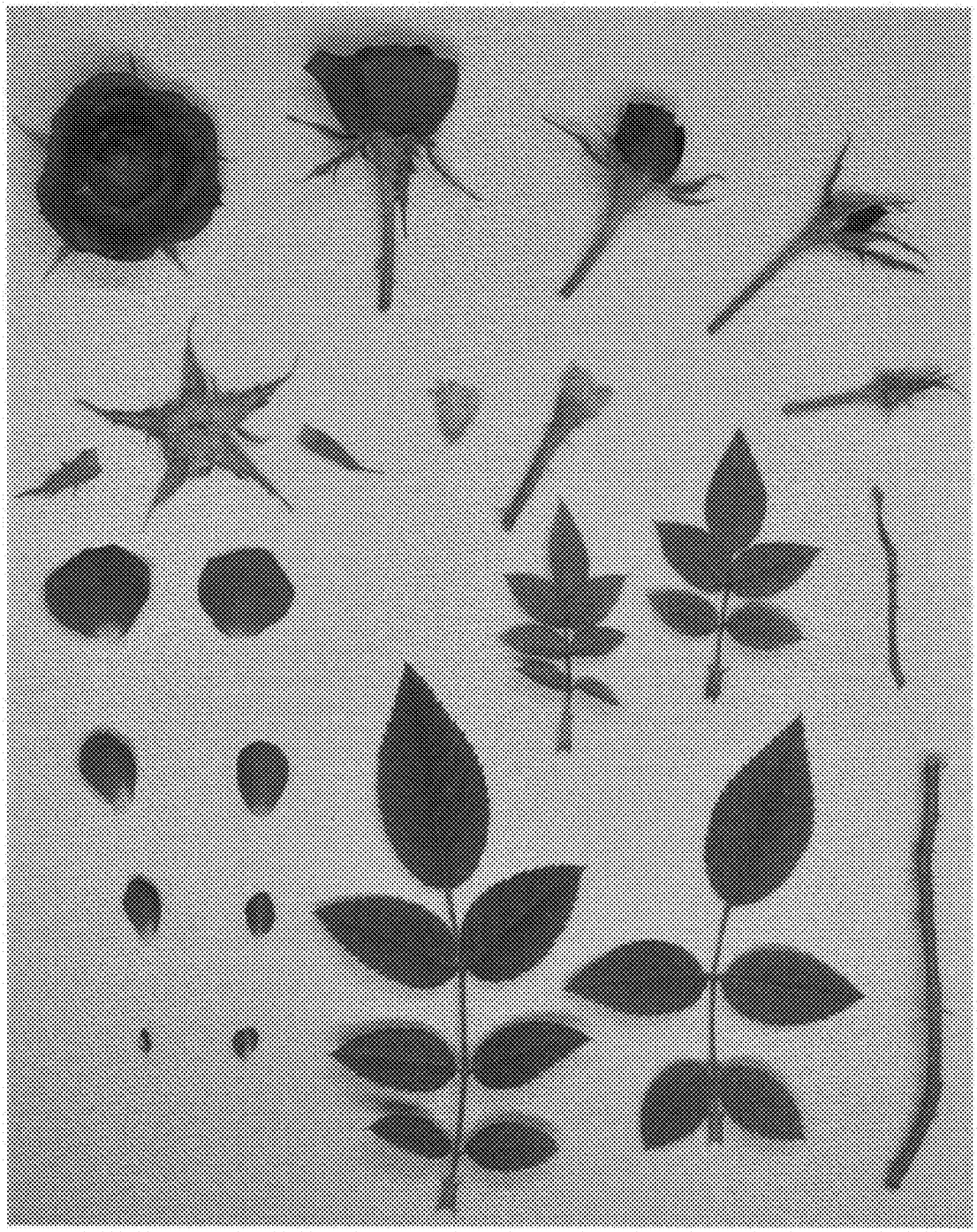
FIG.2 shows a close-up of the individual parts of 4 month old plant observed and growing in a nursery in Jackson County, Oreg.

The following is a description of 'KORpot040', as observed growing in November 2014 in a nursery in Jackson County, Oreg. on plants of 4 months of age. Color references are made using The Royal Horticultural Society (London, England) Colour Chart, 2001 except where common terms of color are used.

Classification:

*Family*.—Rosaceae.

*Species*.—*Rosa hybrida*.

*Common name*.—Miniature rose.

*Variety*.—'KORpot040'.

Parentage:

*Female parent*.—Un-named rose plant (unpatented).

*Male parent*.—Un-named rose plant (unpatented).

Plant:

*Growth*.—Moderately vigorous.

*Habit*.—Compact; upright to bushy.

*Size*.—When grown as a 10.5 cm pot plant, the average plant height is 15.0 cm to 25.0 cm and the average plant width is 15.0 cm to 20.0 cm.

*Winter hardiness*.—Due to the variety's principal use in greenhouses, winter hardiness has not been evaluated.

Stems:

*Color*.—Young wood: RHS 144A (Yellow-Green). Older wood: RHS 146B (Yellow-Green). Intonations: RHS 182A (Greyed-Red) present on youngest wood only.

*Stem surface texture*.—Young and old wood are hispid.

*Length*.—20.0 mm to 23.0 mm average length when grown under commercial greenhouse floral production.

*Diameter*.—Average is 3.0 mm.

Prickles:

*Quantity*.—Abundant; average of 25 to 30 large prickles with an additional 60 or more small prickles per each 10 cm of stem.

*Shape*.—Linear.

*Size*.—Average length of large prickles is 4.0 mm and average length of small prickles is 1.0 mm to 2 mm.

*Color*.—Immature prickles: RHS 145C (Yellow-Green) with anthocyanin intonations of RHS 182A (Greyed-Red). Mature prickles: RHS 145C (Yellow-Green) with anthocyanin intonations of RHS 182D (Greyed-Red).

Leaves:

*General*.—Normally 5 to7 leaflets on normal leaves in middle of the stem.

*Venation pattern*.—Pyramidal net pattern.

*Leaf size*.—110.0 mm to 130.0 mm in length and 60.0 mm to 70.0 mm in width.

*Abundance*.—Very abundant.

Leaflets:

*Size*.—Average size of the terminal leaflet is 40.0 mm to 55.0 mm in length and 20.0 mm to 25.0 mm in width.

*Shape*.—Ovate.

*Base*.—Obtuse.

*Apex*.—Acute.

*Margins*.—Serrated.

*Surface appearance*.—Upper side: Semi-glossy. Under side: Matte.

*Texture*.—Upper side: Smooth. Under side: Leathery.

*Color, mature foliage*.—Upper surface: RHS 137A (Green) and RHS 139A (Green). Lower surface: RHS 147B (Yellow-Green).

*Color, immature foliage*.—Upper surface: RHS 141A (Yellow-Green). Lower surface: RHS 146B (Yellow-Green).

*Color, most immature foliage*.—Upper surface: RHS 144A (Yellow-Green). Lower surface: RHS 146B (Yellow-Green). Anthocyanin intonation: RHS 178A (Greyed-Red) present on leaflet margins and lower surfaces of most immature foliage.

*Arrangement*.—Odd pinnate.

*Venation*.—Reticulate.

*Stipules*.—Size: 12.0 mm in length and 4.0 mm to 5.0 mm in width. Color: RHS 146C (Yellow-Green). Anthocyanin: RHS 182C (Greyed-Red) minimally present on upper surface of midrib and on stipitate glands. Stipitate glands: Abundant on margins. Margins: Glandular toothed. Texture: Glabrous. Apex: Apiculate. Base: Winged.

*Petiole*.—Length: Average is 18.0 mm to 23.0 mm. Diameter: Average is 1.0 mm to 1.5 mm. Color: Upper side: RHS 146B (Yellow-Green). Underneath: RHS 146C (Yellow-Green). Margins: Glandular toothed, with limited numbers of stipitate glands. Anthocyanin: RHS 182A (Greyed-Red) on margins and upper surface of midrib. Prickles: None observed. Stipitate glands: Limited numbers of stipitate glands present on margins. Texture: Upper surface is papillate with light pubescence while underneath is glabrous.

*Petiole rachis*.—Length: Average is 18.0 mm to 23.0 mm. Diameter: Average is 1.0 mm to 1.5 mm. Color: Upper surface: RHS 146B (Yellow-Green). Underneath: RHS 146C (Yellow-Green). Anthocyanin: RHS 182A (Greyed-Red) present on upper surface of midrib, margins, stipitate glands, and prickles. Margins: Glandular toothed. Prickles: A few small prickles underneath. Stipitate glands: Limited numbers of stipitate glands on margins and underneath.

Flower bud:

*Size*.—Upon opening, 20.0 mm to 25.0 mm in length from base of receptacle to distal end of bud and 10.0 mm to 15.0 mm diameter at its widest point.

*Form*.—Long; pointed ovoid.

*Color*.—As the sepals first unfold, the bud color is RHS 59A (Red-Purple) and RHS 60A (Red-Purple); when one-quarter open, the upper surface of the petals is RHS 53A (Red) and the lower surface is RHS 46A (Red).

Sepals:

*Color*.—Upper surface: RHS 144A (Yellow-Green) with intonations of RHS 144B (Yellow-Green) on the base. Lower surface: RHS 144A (Yellow-Green).

*Size*.—Average is 20.0 mm to 27.0 mm for the length and 5.0 mm to 7.0 mm for the width.

*Shape*.—Strong foliaceous appendages on 3 of the five sepals.

*Apex*.—Apiculate.

*Base*.—Flat at union with receptacle.

*Quantity*.—Five.

*Surface texture*.—Upper side: Hoary. Lower surface: Hispid.

*Margins*.—Cilliate and glandular toothed margins observed.

*Stipitate glands*.—Abundant numbers of stipitate glands on lower surface and some margins.

Flower:

*Blooming habit*.—Recurrent; floriferous.

*General*.—Multiple flower buds per inflorescence, generally 1 to 3; occasionally, 1 flowering lateral present below initiation of the inflorescence, typically 1 flower per lateral; flowers held upright.

*Fragrance*.—Absent.

*Duration*.—On the plant 15 to 20 days; senesced petals drop away cleanly.

*Size*.—Medium for a miniature rose; when open, the average flower diameter is 40.0 mm to 45.0 mm and the average flower height is 25.0 mm.

*Overall shape*.—Round.

*Shape of flower when viewed from the side*.—Upon opening, upper part and lower part: Flattened convex. Open flower, upper part and lower part: Flattened convex.

*Color*.—Upon opening, petals: Outermost petals: Outer side and inner side: RHS 46A (Red). Innermost petals: Outer side: RHS 46A (Red) and RHS 53A (Red), with intonations of RHS 155C (White) occasionally present on midrib. Inner side: RHS 46A (Red) and RHS 53A (Red). Upon opening, basal petal spots: Basal petal spot, outermost petals: Outer side: RHS 155C (White). Inner side: RHS 155C (White). Size: Average is 2.0 mm to 4.0 mm in height and 3.0 mm to 5.0 mm in width. Basal petal spot, innermost petals: Outer side and inner side: RHS 155C (White). Size: Average is 2.0 mm to 5.0 mm in height and 2.0 mm to 3.0 mm in width. After opening, petals: Outermost petals: Outer side: RHS 60A (Red-Purple). Inner side: RHS 46A (Red). Innermost petals: Outer side: RHS 60A (Red-Purple), with intonations of RHS 155C (White) occasionally present on midrib. Inner side: RHS 46A (Red). After opening, basal petal spots: Basal petal spot, outermost petals: Outer side and inner side: RHS 155C (White). Size: Average is 2.0 mm to 5.0 mm in height and 3.0 mm to 5.0 mm in width. Basal petal spot, innermost petals: Outer side: RHS 155C (White). Inner side: RHS 155C (White). Size: Average is 3.0 mm to 5.0 mm in height and 2.0 mm to 3.0 mm in width.

*General tonality*.—On open flowers, RHS 46A (Red); no change in the general tonality at the end of the eighth day; afterwards, general tonality is RHS 46C (Red).

*Petals*.—Petal count: Very double; approximately 75 petals under normal conditions. Petal reflex: Outermost petals reflex very slightly; reflex occurs one by one. Shape: Outermost petals are obovate and innermost petals are elliptic. Apex: Outermost petals obtuse and innermost petals are acute. Base: Outermost and innermost petals are cuneate. Margin: Entire. Petal size: 10.0 mm to 24.0 mm in length and 6.0 mm to 26.0 mm in width. Petal arrangement: Formal. Texture: Upper and lower surfaces are leathery.

*Pedicel*.—Surface: Abundant stipitate glands and small prickles. Length: 45.0 mm to 65.0 mm average. Diameter: 2.0 mm to 4.0 mm average. Color: RHS 144A (Yellow-Green). Strength: Strong. Texture: Hispid.

*Peduncle*.—Surface: Abundant stipitate glands and small prickles. Length: 25.0 mm to 65.0 mm average. Diameter: 2.0 mm to 3.0 mm average. Color: RHS 144A (Yellow-Green). Strength: Strong.

Petaloids:

*Petaloid count*.—Average of 20 per flower.

*Size*.—7.0 mm to 10.0 mm in length and 3.0 mm to 6.0 mm in width.

*Color*.—Inner side: RHS 53A (Red) on marginal and middle zones, RHS 155A (White) on basal zone and intonations on midrib. Outer side: RHS 53A (Red) on marginal and middle zones, RHS 155A (White) on basal zone and intonations on midrib.

*Texture*.—Inner side and outer side are smooth.

*Margins*.—Entire and undulated petaloid margins observed.

*Shape*.—Most commonly obovate with some petaloids highly irregular.

*Apex*.—Obtuse.

*Base*.—Attenuate.

Reproductive organs:

*Pistils*.—Quantity: Average is approximately 60 present. Stigmas: Location: Slightly superior to equal in position to anthers. Color: RHS 158C (Yellow-White). Diameter: 0.5 mm to 1.0 mm. Styles: Length: About 5.0 mm to 6.0 mm. Color: RHS 158A (Yellow-White), with intonations of RHS 52C (Red).

*Stamens*.—Quantity: Approximately 60 on average and regularly arranged. Anthers: Size: Average is 3.0 mm in length and 1.5 mm in width. Pollen: Generally present. Color: RHS 163B (Greyed-Orange). Filaments: Color: RHS 5A (Yellow). Length: 3.0 mm to 5.0 mm.

*Receptacle*.—Surface: Abundant stipitate glands and small prickles. Color: RHS 144B (Yellow-Green). Shape: Urn-shaped. Texture: Hispid. Size: 5.0 mm to 6.0 mm in height and 6.0 mm to 8.0 mm in width.

Hips and seed formation: None observed.

Disease resistance: Above average resistance to Powdery mildew (*Sphaerotheca pannosa*) and Botrytis (*Botrytis cinerea*) diseases under normal growing conditions in Jackson County, Oreg.

COMPARISON WITH PARENTAL LINES

The new rose plant may be distinguished from the female or seed parent, an un-named seedling, by the following combination of characteristics:

1. 'KORpot040' has more flowers with longer durability than the female parent.
2. 'KORpot040' has less vigorous, more compact growth than the female parent.

The new rose plant may be distinguished from the male or pollen parent, an un-named seedling, by the following combination of characteristics:

1. 'KORpot040' has dark red flowers, whereas the male parent has hot-pink colored flowers.

2. 'KORpot040' has medium-sized flowers for a miniature rose, whereas the male parent has large flowers.

When 'KORpot040' is compared to the commercial comparison rose variety 'KORhedani' (U.S. Plant Pat. No. 19,598), the following differences are noted in Table 1.

TABLE 1

| Characteristic | 'KORpot040' | 'KORhedani' |
|---|---|---|
| Petal count | Approximately 75 petals under normal conditions. | Approximately 30 to 32 petals under normal conditions |

TABLE 1-continued

| Characteristic | 'KORpot040' | 'KORhedani' |
|---|---|---|
| Average number of prickles per 10.0 cm of stem | 25 to 30 large prickles, and upwards of 60 small prickles. | Less than 1 |
| Average open flower diameter | 40.0 mm to 45.0 mm | 55 mm |

I claim:

1. A new and distinct variety of rose plant designated 'KORpot040' as illustrated and described herein.

* * * * *